(12) United States Patent
Sauer et al.

(10) Patent No.: US 6,612,991 B2
(45) Date of Patent: Sep. 2, 2003

(54) VIDEO-ASSISTANCE FOR ULTRASOUND GUIDED NEEDLE BIOPSY

(75) Inventors: Frank Sauer, Princeton, NJ (US); Ali Khamene, Plainsboro, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 10/222,170

(22) Filed: Aug. 16, 2002

(65) Prior Publication Data

US 2003/0120155 A1 Jun. 26, 2003

Related U.S. Application Data

(60) Provisional application No. 60/312,872, filed on Aug. 16, 2001, provisional application No. 60/312,876, filed on Aug. 16, 2001, provisional application No. 60/312,871, filed on Aug. 16, 2001, provisional application No. 60/312,875, filed on Aug. 16, 2001, and provisional application No. 60/312,873, filed on Aug. 16, 2001.

(51) Int. Cl.$^7$ .................................................. A61B 8/00
(52) U.S. Cl. ...................................... 600/461; 600/437
(58) Field of Search .................. 600/437, 461, 600/407, 439, 547, 477, 478, 476; 606/170, 180, 159; 348/65

(56) References Cited

U.S. PATENT DOCUMENTS

| | | | | | |
|---|---|---|---|---|---|
| 5,492,126 | A | * | 2/1996 | Hennige et al. | 600/439 |
| 5,527,331 | A | * | 6/1996 | Kresch et al. | 606/170 |
| 5,617,858 | A | * | 4/1997 | Taverna et al. | 600/407 |
| 5,647,373 | A | * | 7/1997 | Paltieli | 600/567 |
| 5,810,742 | A | * | 9/1998 | Pearlman | 600/547 |

* cited by examiner

Primary Examiner—Marvin M. Lateef
Assistant Examiner—Ruby Jain
(74) Attorney, Agent, or Firm—Donald B. Paschburg

(57) ABSTRACT

A method for video assistance for ultrasound guided needle biopsy of a patient, includes the steps of obtaining an ultrasound image of said patient in an ultrasound imaging plane by way of a transducer head; obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image; and overlaying graphic markers onto said video image for indicating said ultrasound imaging plane as a line of possible entry points for needle biopsy.

27 Claims, 1 Drawing Sheet

VIDEO-ASSISTANCE FOR ULTRASOUND GUIDED NEEDLE BIOPSY

Figure 1:
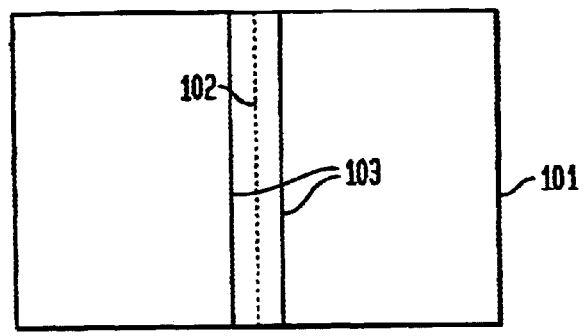

Reference is hereby made to the following U.S. Provisional patent applications whereof the benefit is hereby claimed and the disclosures hereby incorporated by reference:

U.S. Provisional patent application No. 60/312.872, entitled MARKING 3D LOCATIONS FROM ULTRASOUND IMAGES and filed Aug. 16, 2001 in the names of Frank Sauer, Ali Khamene, Benedicte Bascle;

U.S. Provisional patent application No. 60/312,876, entitled LOCAL 3D RECONSTRUCTION FROM ULTRASOUND IMAGES and filed Aug. 16, 2001 in the names of Frank Sauer, Ali Khamene, Benedicte Bascle;

U.S. Provisional patent application No. 60/312,871, entitled SPATIOTEMPORAL FREEZING OF ULTRASOUND IMAGES IN AUGMENTED REALITY VISUALIZATION and filed Aug. 16, 2001 in the names of Frank Sauer, Ali Khamene, Benedicte Bascle;

U.S. Provisional patent application No. 60/312,875, entitled USER INTERFACE FOR AUGMENTED AND VIRTUAL REALITY SYSTEMS and filed Aug. 16, 2001 in the names of Frank Sauer, Lars Schimmang, Ali Khamene; and U.S. Provisional patent application No. 60/312,873, entitled VIDEO-ASSISTANCE FOR ULTRASOUND GUIDED NEEDLE BIOPSY and filed Aug. 16, 2001 in the names of Frank Sauer and Ali Khamene.

Reference is hereby made to the following copending U.S. patent applications being filed on even date herewith.

U.S. patent application, entitled MARKING 3D LOCATIONS FROM ULTRASOUND IMAGES filed in the names of Frank Sauer, Ali Khamene, Benedicte Bascle;

U.S. patent application entitled LOCAL 3D RECONSTRUCTION FROM ULTRASOUND IMAGES and filed in the names of Frank Sauer, Ali Khamene, Benedicte Bascle;

U.S. patent application entitled SPATIOTEMPORAL FREEZING OF ULTRASOUND IMAGES IN AUGMENTED REALITY VISUALIZATION and filed in the names of Frank Sauer, Ali Khamene, Benedicte Bascle; and U.S. patent application entitled USER INTERFACE FOR AUGMENTED AND VIRTUAL REALITY SYSTEMS and filed in the names of Frank Sauer, Lars Schimmang, Ali Khamene.

The present invention relates to the field of guidance for the insertion of a biopsy needle and, more specifically to providing assistance for ultrasound guided needle biopsy.

For a needle biopsy, a biopsy needle has to be inserted into an anatomical target to remove a tissue sample. Ultrasound guidance is routinely used, for example, for breast needle biopsies. The real-time ultrasound images allow the physician to locate the target and to monitor the needle position.

Typically, the procedure is performed "in-plane", that is, the ultrasound imaging is performed in a plane. In accordance with known procedures, with the ultrasound transducer being in a position where the target is visible in the image, the insertion point of the needle is chosen on the intersection of the ultrasound plane and the patient's skin surface. The needle is oriented so that it lies in this plane and points towards the target. When the needle is now inserted, it will appear in the ultrasound image, and the progress along its path towards the target can be monitored.

One difficulty with performing an ultrasound guided needle biopsy in this way is to correctly position and orient the needle to be in the same plane with the ultrasound image. Mechanical needle guides are commercially available to facilitate this task. They are clipped onto the transducer and constrain the movement of the needle so that it is forced to stay in a plane aligned with the transducer. Even though the needle can now reliably be placed in the plane of the ultrasound image, many physicians find the rigid constraint imposed by the use of this mechanical guide too inflexible and consequently do not use it. They want to be able to make corrective adjustments to the path of the needle as it approaches the target, and this is not easily possible with the constraints of the mechanical needle guide. Nor is it possible to insert the needle at some distance from the ultrasound imaging transducer, which is desirable for shallow needle angles because the mechanical guide constrains the needle entry point to be close to the transducer.

It is an object of the present invention to makes in-plane needle alignment easy while preserving the full flexibility of a free-hand procedure.

A method for video assistance for ultrasound guided needle biopsy of a patient, includes the steps of obtaining an ultrasound image of said patient in an ultrasound imaging plane by way of a transducer head; obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image; and overlaying graphic markers onto said video image for indicating said ultrasound imaging plane as a line of possible entry points for needle biopsy.

In accordance with another aspect of the invention, apparatus for video assistance for ultrasound guided needle biopsy of a patient, comprises: ultrasound imaging apparatus, the imaging apparatus including a transducer head for obtaining ultrasound data from the patient in an ultrasound imaging plane for forming an ultrasound image of actual anatomical structures in the patient; a video camera mounted on the transducer head for obtaining a body surface video image of the patient including an area wherein the ultrasound imaging plane intersects said body surface, the video camera having an optical axis lying in said ultrasound imaging plane such that the ultrasound imaging plane corresponds to a line in the video image; graphic markers overlaid onto said video image for indicating said ultrasound imaging plane as a line of possible entry points for needle biopsy; and an augmented reality visualization system coupled to their ultrasound imaging apparatus for providing augmented images enabling visible structures in the ultrasound image to appear in the location of corresponding ones of the actual anatomical structures.

Figure 2:
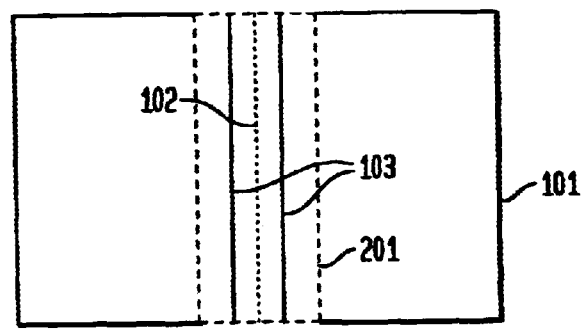
Figure 3:
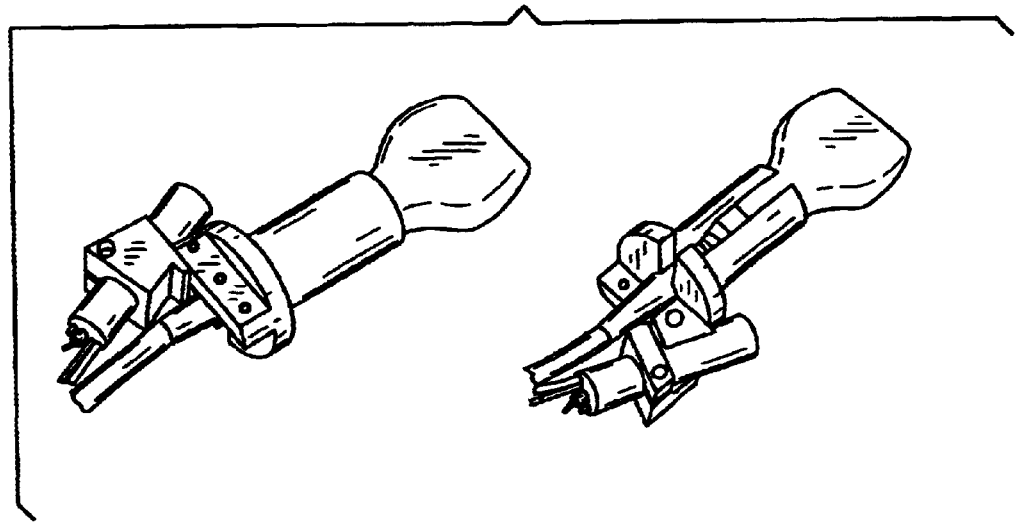

The invention will be more fully understood from the description of preferred embodiments which follows in conjunction with the Drawing, in which FIGS. 1 and 2 show graphical guides marking the location of the ultrasound plane in accordance with an embodiment of the present invention; and FIG. 3 shows an illustrative simulation of a mounting usable for mounting a camera onto an ultrasound transducer in accordance with the principles of the present invention.

The term "ultrasound plane" or "ultrasound imaging plane" as used herein denotes the plane, determined by the pose and geometry of the ultrasound transducer, in which the ultrasound system collects image data.

In accordance with an illustrative embodiment of the present invention, an ultrasound imaging system includes a transducer and a display monitor. A miniature video camera is attached to the transducer in a downward-looking pose.

The camera's optical axis lies in the ultrasound imaging plane of the transducer, so that the ultrasound plane corresponds to a line in the video image. Preferably, the camera is aligned around its optical axis such that this line is oriented either vertically or horizontally in the video image. Preferably, graphics is overlaid onto the video image to mark the location of the line, as shown in FIG. 1. FIG. 1 shows: a graphics overlay for video image 101; 102: line corresponding to ultrasound plane; 103: graphical guides that mark the location of the ultrasound plane.

The camera provides the user with an image of a "bird's eye view" of the transducer head and the region on the patient where the needle will be inserted. Graphical markers in the image tell the user the location of the ultrasound transducer plane. Accordingly, the user can easily choose a needle entry point that lies in the ultrasound imaging plane and can further align the whole needle to lie in this plane, by aligning the needle as seen in the video image with the markers overlaid onto the video image. During needle insertion, the correct "in-plane" needle alignment can be monitored on the video image.

It is herein recognized that there is no essential need to display the full video image. Generally, it is sufficient to display a region of interest that includes the ultrasound plane. See FIG. 2. For alignment purposes, it is sufficient to show only part of the whole video image 101, for example the region-of-interest 201 that contains the ultrasound plane and the graphical markers.

The video image from the camera can be displayed on a separate monitor or, optionally, it may be shown as an inset on the ultrasound system's monitor, depending on convenience and the type of application being used.

Augmented reality visualization techniques are known wherein ultrasound images are overlaid onto a view of the patient with registration of visualized structures and the corresponding physical structures. In accordance with an embodiment of the present invention, the ultrasound system is combined with an augmented reality visualization system, with which the user observes the ultrasound images in-situ, overlaid onto the user's view of the patient, registered in a way that structures seen in the ultrasound images appear in the location of the actual anatomical structures. In a preferred embodiment, the user wears a head-mounted display to watch these augmented images. In this embodiment, the video image that facilitates the in-plane needle alignment is preferably shown as an inset in these augmented images.

A mechanical mounting is desirable for enabling placement of the optical axis of the video camera in the plane of ultrasound imaging in such a way that the plane of ultrasound imaging corresponds to either to the horizontal or vertical direction in the video image.

In accordance with an embodiment of the present invention, a camera body has a cylindrical shape so that a mounting designed for cooperative engagement therewith is used to hold the camera such that only the orientation of the camera's axis is defined. Thus, in an alignment step, the camera is turned or adjusted around its axis until the ultrasound plane corresponds to a vertical or a horizontal direction in the video image.

FIG. 3 shows a mechanical mounting comprising essentially a hollow cylindrical receptacle for clasping a cylindrical body. While the arrangement shown in FIG. 3 actually happens to be a mounting for a cylindrical laser device on an ultrasound transducer, it is used herein nevertheless, being conveniently suitable for illustrating the principle of an essentially similar mounting for holding a cylindrical video camera. The mounting may be integrally formed in the transducer handle or it may be in the form of separate unit with a slotted hollow cylindrical adapter portion for allowing the cylindrical portion to fit and slide over the handle of the transducer to serve as a base for the video camera mount. In FIG. 3, the two photos show a laser with line projection optics mounted onto an ultrasound transducer. The mount comprises a hollow cylinder that fits on the transducer's handle. The slit on the cylinder's back allows one to insert the cylinder over the transducer cable before moving it down onto the handle. The cylinder has an upper platform to which the actual laser mount is attached.

A similar mechanical mount can be used to hold the video camera described in the present invention. In particular, if the camera is of the "lipstick" variety, i.e. has a cylindrical body, the mechanical mount would only need to be adapted from the laser diameter to the diameter of the camera.

In another embodiment of the present invention, a simple mirror-image modification is provided for the convenience of left-handed and right-handed users by using a reversible adapter. Alternatively, separate cameras for left and right handed use can provide a solution.

While the invention has been explained by way of exemplary embodiments, it will be understood by one of skill in the art to which it pertains that various modifications and changes may be readily made without departing from the spirit of the invention which is defined by the claims following.

What is claimed is:

1. Apparatus for video assistance for ultrasound guided needle biopsy of a patient, comprising:
   ultrasound imaging apparatus, said imaging apparatus including a transducer head for obtaining image data from said patient in an ultrasound imaging plane;
   a video camera mounted on said transducer head for obtaining a body surface video image of said patient including an area wherein said ultrasound imaging plane intersects said body surface, said video camera having an optical axis lying in said ultrasound imaging plane such that said ultrasound imaging plane corresponds to a line in said video image; and
   graphic markers overlaid onto said video image for indicating said ultrasound imaging plane as a line of possible entry points for needle biopsy.

2. Apparatus for video assistance as recited in claim 1, wherein said video camera has an optical axis lying in said ultrasound imaging plane such that said ultrasound imaging plane corresponds to a line in said video image having one of a horizontal and a vertical orientation.

3. Apparatus for video assistance as recited in claim 2, wherein said video camera is detachably mounted on said transducer head with freedom of rotation about an axis corresponding approximately to said optical axis.

4. Apparatus for video assistance as recited in claim 2, wherein said video camera is rotatably mounted on said transducer head with freedom of rotation about an axis corresponding approximately to said optical axis.

5. Apparatus for video assistance as recited in claim 4, wherein said video camera is rotatably mounted on said transducer head by way of a friction mounting.

6. Apparatus for video assistance as recited in claim 4, wherein said video camera is rotatably mounted on said transducer head by way of an optionally clamping mounting.

7. Apparatus for video assistance as recited in claim 2, wherein said video camera is is of an integral construction with said transducer head with freedom of rotation about an axis corresponding approximately to said optical axis.

8. Apparatus for video assistance as recited in claim 7, wherein said integral construction provides said video camera with freedom of rotation about an axis corresponding approximately to said optical axis.

9. Apparatus for video assistance as recited in claim 8, wherein said freedom of rotation is provided by way of a friction mounting.

10. Apparatus for video assistance as recited in claim 8, wherein said freedom of rotation is provided by way of an optionally clamping mounting.

11. Apparatus for video assistance for ultrasound guided needle biopsy of a patient, comprising:

ultrasound imaging apparatus, said imaging apparatus including a transducer head for obtaining ultrasound image data from said patient in an ultrasound imaging plane;

a video camera mounted on said transducer head for obtaining a body surface video image of said patient including an area wherein said ultrasound imaging plane intersects said body surface, said video camera having an optical axis lying in said ultrasound imaging plane such that said ultrasound imaging plane corresponds to a line in said video image;

an image monitor screen for displaying said ultrasound image data and for displaying said video image as an inset image to said ultrasound image data; and graphic markers overlaid onto said video image for indicating said ultrasound imaging plane as a line of possible entry points for needle biopsy.

12. Apparatus for video assistance for ultrasound guided needle biopsy of a patient, comprising:

ultrasound imaging apparatus, said imaging apparatus including a transducer head for obtaining ultrasound data from said patient in an ultrasound imaging plane for forming an ultrasound image of actual anatomical structures in said patient;

a video camera mounted on said transducer head for obtaining a body surface video image of said patient including an area wherein said ultrasound imaging plane intersects said body surface, said video camera having an optical axis lying in said ultrasound imaging plane such that said ultrasound imaging plane corresponds to a line in said video image;

graphic markers overlaid onto said video image for indicating said ultrasound imaging plane as a line of possible entry points for needle biopsy;

an augmented reality visualization system coupled to said ultrasound imaging apparatus for providing augmented images enabling visible structures in said ultrasound image to appear in the location of corresponding ones of said actual anatomical structures.

13. Apparatus for video assistance as recited in claim 12, including a head-mounted display for displaying said augmented images.

14. Apparatus for video assistance as recited in claim 12, wherein said video image appears as an inset to said augmented images.

15. A method for video assistance for ultrasound guided needle biopsy of a patient, comprising the steps of:

obtaining an ultrasound image of said patient in an ultrasound imaging plane by way of a transducer head;

obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image; and overlaying graphic markers onto said video image for indicating said ultrasound imaging plane as a line of possible entry points for needle biopsy.

16. A method for video assistance as recited in claim 15, including the step of adjusting said optical axis such that said line in said video image exhibits one of a horizontal and a vertical orientation.

17. A method for video assistance as recited in claim 16, wherein said step of adjusting said optical axis includes rotating said transducer head about an axis corresponding approximately to said optical axis.

18. A method for video assistance for ultrasound guided needle biopsy of a patient, comprising the steps of:

obtaining an ultrasound image of said patient in an ultrasound imaging plane by way of a transducer head;

obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image;

overlaying graphic markers onto said video image for indicating said ultrasound imaging plane as a line of possible entry points for needle biopsy; and providing an augmented ultrasound image for enabling visible structures in said ultrasound image to appear in the location of corresponding ones of said actual anatomical structures by way of an augmented reality visualization system coupled to said ultrasound imaging apparatus.

19. A method for video assistance as recited in claim 18, including a step of adjusting an optical axis of said video camera lying in said ultrasound imaging plane such that said ultrasound imaging plane corresponds to a line in said video image having one of a horizontal and a vertical orientation.

20. A method for video assistance as recited in claim 18, including a step of displaying said augmented images in a head-mounted display.

21. Apparatus for video assistance for ultrasound guided needle biopsy of a patient, comprising:

means for obtaining an ultrasound image of said patient in an ultrasound imaging plane by way of a transducer head;

means for obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image; and means for overlaying graphic markers onto said video image for indicating said ultrasound imaging plane as a line of possible entry points for needle biopsy.

22. Apparatus for video assistance as recited in claim 21, comprising means for adjusting said optical axis such that said line in said video image exhibits one of a horizontal and a vertical orientation.

23. Apparatus for video assistance as recited in claim 21, comprising means allowing adjustment of said optical axis by rotating said transducer head about an axis corresponding approximately to said optical axis.

24. Apparatus for video assistance for ultrasound guided needle biopsy of a patient, comprising:

means for obtaining an ultrasound image of said patient in an ultrasound imaging plane by way of a transducer head;

means for obtaining a body surface video image of said patient including an area wherein said ultrasound imaging plane intersects said body surface, by way of a video camera mounted on said transducer head and having an optical axis lying in said ultrasound imaging plane such that said ultrasound imaging plane corresponds to a line in said video image;

means for overlaying graphic markers onto said video image for indicating said ultrasound imaging plane as a line of possible entry points for needle biopsy; and means for providing an augmented ultrasound image for enabling visible structures in said ultrasound image to appear in the location of corresponding ones of said actual anatomical structures by way of an augmented reality visualization system coupled to said ultrasound imaging apparatus.

25. Apparatus for video assistance as recited in claim 24, including means allowing adjustment adjusting an optical axis of said video camera lying in said ultrasound imaging plane such that said ultrasound imaging plane corresponds to a line in said video image having one of a horizontal and a vertical orientation.

26. Apparatus method for video assistance as recited in claim 24, including a step of displaying said augmented images in a head-mounted display.

27. Apparatus for video assistance as recited in claim 24, including a step of displaying said video image as an inset to said augmented images.

* * * * *